United States Patent [19]
Selliah et al.

[11] Patent Number: 6,025,392
[45] Date of Patent: *Feb. 15, 2000

[54] SUBSTITUTED TETRAHYDROFURAN ANALOGS OF PROSTAGLANDINS AS OCULAR HYPOTENSIVES

[75] Inventors: Robert D. Selliah, Fort Worth; Mark R. Hellberg, Arlington; Peter G. Klimko, Fort Worth; Verney L. Sallee, Burleson; Paul W. Zinke, Fort Worth, all of Tex.

[73] Assignee: Alcon Laboratories, Inc., Fort Worth, Tex.

[ * ] Notice: This patent is subject to a terminal disclaimer.

[21] Appl. No.: 09/109,852

[22] Filed: Jul. 2, 1998

Related U.S. Application Data

[63] Continuation-in-part of application No. 08/809,920, filed as application No. PCT/US96/17900, Nov. 12, 1996
[60] Provisional application No. 60/009,866, Dec. 22, 1995.

[51] Int. Cl.[7] .......................... A61K 31/34; C07D 307/20
[52] U.S. Cl. .......................... 514/473; 549/475; 549/497; 549/504
[58] Field of Search ..................... 549/475, 497, 549/504; 514/473

[56] References Cited

U.S. PATENT DOCUMENTS

| | | | |
|---|---|---|---|
| 3,883,659 | 5/1975 | Vlattas | 424/285 |
| 4,088,779 | 5/1978 | Vlattas | 424/285 |
| 4,133,817 | 1/1979 | Lourens et al. | 260/340.9 R |
| 5,574,066 | 11/1996 | Chan et al. | 514/548 |

FOREIGN PATENT DOCUMENTS

| | | |
|---|---|---|
| 0667160 A2 | 8/1995 | European Pat. Off. . |
| 0686628 A2 | 12/1995 | European Pat. Off. . |
| 2460977 | 7/1976 | Germany . |
| 2601333 | 7/1976 | Germany . |
| 2618861 | 11/1976 | Germany . |
| 2739277 | 3/1978 | Germany . |
| 1458164 | 12/1976 | United Kingdom . |
| 1539364 | 1/1979 | United Kingdom . |
| WO 95/26729 | 10/1995 | WIPO . |

OTHER PUBLICATIONS

Alm, "The Potential of Prostaglandin Derivatives in Glaucoma Therapy" *Current Opinion in Ophthalmology* 4(II):44–50 (1993).

Arndt et al., "Stereospecific Synthesis of Modified Prostaglandins Derived from Carbohydrates. Part 1." *S. Afr. J. Chem.* 34(4):121–127 (Jun. 1981).

Giuffre, "The Effects of Prostaglandin $F_{2\alpha}$ in the Human Eye" *Graefe's Arch Clin Exp Ophthalmol* 222:139–141 (1985).

Hanessian et al., "Total Synthesis of 11–Oxaprostaglandin $F_{2\alpha}$ and $F_{2\beta}$," *Carbohydrate Research* 141:221–238 (1985).

Kerstetter et al., "Prostaglandin $F_{2\alpha}$–1–Isopropylester Lowers Intracular Pressure Without Decreasing Aqueous Humor Flow" *American Journal of Ophthalmology* 105:30–34 (1988).

Lourens et al., "The Novel Stereospecific Synthesis of 11–Oxaprostaglandin $F_{2\alpha}$," *Tetrahedron Letters*, No. 43:3719–3722 Pergamon Press XP000644760 (1975).

Nakajima et al., "Effects of Prostaglandin $D_2$ and its Analogue, BW245C, on Intraocular Pressure in Humans" *Graefe's Arch Clin Exp Ophthalmol* 229:411–413 (1991).

Thiem et al., "Synthese von Oxaprostaglandinen aus 1,4:3,6–Dianhydro–D–sorbit" *Liebigs Ann. Chem.* 2151:2164 XP000644761 (1985).

Thierauch et al., "Prostaglandins and Their Receptors: II. Receptor Structure and Signal Transduction" *Journal of Hypertension* 12:1–5 (1994).

Verdoorn et al., "Synthesis of Methyl (5Z, 13E)(15S)–9α–acetoxy–15–hydroxy–17–(3–trifluoromethylphenyl)–11–oxa–18,19,20–trinorprosta–5,13–dienoate" *S. Afr. Tydskr. Chem.* 40(2):134–138 (1987).

Vlattas et al., "Synthesis of 9–Oxaprostaglandins" *Tetrahedron Letters* No. 51/52:4455–4458, Pergamon Press, 1974.

Vlattas et al., "Synthesis of 11–Oxaprostaglandins" *Tetrahedron Letters* No. 51/52:4451–4454, XP000644759, Pergamon Press, 1974.

*Primary Examiner*—Ba K. Trinh
*Attorney, Agent, or Firm*—Barry L. Copeland

[57] ABSTRACT

Substituted tetrahydrofuran analogs of F-series prostaglandins and methods of their use in treating glaucoma and ocular hypertension are disclosed.

16 Claims, No Drawings

SUBSTITUTED TETRAHYDROFURAN ANALOGS OF PROSTAGLANDINS AS OCULAR HYPOTENSIVES

CROSS REFERENCE TO RELATED APPLICATIONS

This application is a continuation-in-part of U.S. patent application Ser. No. 08/809,920 filed Apr. 4, 1997, a national application under 35 U.S.C. § 371 of PCT Application Ser. No. PCT/US96/17900 filed Nov. 12, 1996, which draws priority from U.S. Provisional Application Ser. No. 60/009,866 filed Dec. 22, 1995, (now abandoned).

BACKGROUND OF THE INVENTION

The present invention relates to novel compounds and compositions, and methods of their use in the treatment of glaucoma and ocular hypertension. In particular, the present invention relates to the use of certain substituted tetrahydrofuran analogs of F series prostaglandins to treat glaucoma and ocular hypertension.

Glaucoma is a progressive disease which leads to optic nerve damage, and, ultimately, total loss of vision. The causes of this disease have been the subject of extensive studies for many years, but still are not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which reduce either the production of aqueous humor within the eye, such as beta-blockers and carbonic anhydrase inhibitors, or increase the flow of aqueous humor out of the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects, such as nausea, dyspepsia, fatigue, and metabolic acidosis, which side effects can affect patient compliance and/or necessitate the termination of treatment. Moreover, some beta-blockers have increasingly become associated with serious pulmonary side effects attributable to their effects on beta-2 receptors in pulmonary tissue. Sympathomimetics may cause tachycardia, arrhythmia and hypertension. There is therefore a continuing need for therapies which control the elevated intraocular pressure associated with glaucoma.

Prostaglandins, which are metabolite derivatives of arachidonic acid, have recently been pursued for possible efficacy in lowering IOP. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F, G, I and J-series prostaglandins (EP 0 561 073 A1). Of interest in the present invention are compounds which are believed to exhibit IOP lowering mechanisms similar to those exhibited by $PGF_{2\alpha}$ (formula (I)):

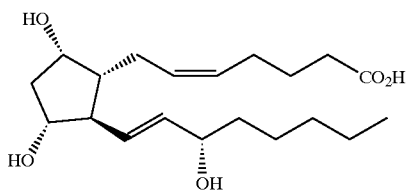

The relationship of prostaglandin FP receptor activation and IOP lowering effects is not well understood. It is believed that FP receptor activation leads to increased outflow of aqueous humor. Regardless of mechanism, $PGF_{2\alpha}$ and some of its analogs have been shown to lower IOP (Giuffre, *The Effects of Prostaglandin $F_{2\alpha}$ the Human Eye*, Graefe's Archive Ophthalmology, volume 222, pages 139–141 (1985); and Kerstetter et al., *Prostaglandin $F_{2\alpha}$-1-Isopropylester Lowers Intraocular Pressure Without Decreasing Aqueous Humor Flow*, American Journal of Ophthalmology, volume 105, pages 30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (*Graefe's Archive Ophthalmology*, volume 229, pages 411–413 (1991)). Though $PGF_{2\alpha}$-type molecules may lower IOP, these types of molecules have also been associated with undesirable side effects resulting from topical ophthalmic dosing. Such effects include an initial increase in IOP, breakdown of the blood aqueous barrier and conjunctival hyperemia (Alm, *The Potential of Prostaglandin Derivatives in Glaucoma Therapy*, Current Opinion in Ophthalmology, volume 4, No. 11, pages 44–50 (1993)).

Based on the foregoing, a need exists for the development of molecules that may activate the prostaglandin FP receptors, yielding a more efficacious lowering of IOP, while exhibiting fewer or reduced side effects. An agent which exhibits comparable or improved efficacy, but with reduced side effects when compared to other agents, is said to have an improved therapeutic profile. It is an object of this invention to provide a class of IOP lowering agents with an improved therapeutic profile over endogenous prostaglandins, and methods of their use.

SUMMARY OF THE INVENTION

The present invention is directed to compositions and methods of their use in treating glaucoma and ocular hypertension. In particular, the present invention provides certain classes of substituted tetrahydrofurans which may possess functional FP receptor agonist activity, and methods of their use in treating glaucoma and ocular hypertension.

DETAILED DESCRIPTION OF THE INVENTION

It has unexpectedly been found that substituted tetrahydrofurans of the present invention exhibit an improved therapeutic profile in the treatment of glaucoma and ocular hypertension when compared to natural prostaglandins and many of their known analogs. The substituted tetrahydrofurans of the present invention are heptanoic acid derivatives having the following formula (II):

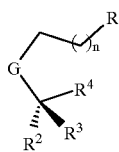

(II)

wherein:

R=pharmaceutically acceptable ester moiety, $CO_2R^1$, $CONR^7R^8$, $CH_2OR^9$, or $CH_2NR^{10}R^{11}$, where $R^1$=H or cationic salt moiety; $R^7$ and $R^8$ are the same or different=H or alkyl; $R^9$=H, acyl, or alkyl; and $R^{10}$ and $R^{11}$ are the same or different=H, acyl, or alkyl; with the proviso that if one of $R^{10}$ and $R^{11}$=acyl, then the other=H or alkyl;

n=0 or 2;

G is:

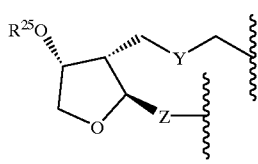

(i)

wherein:

Y=cis $CH_2CH=CH$, cis $CH=CHCH_2$, or $CH_2CH_2CH_2$;
Z=C≡C, trans CH=CH, or $CH_2CH_2$;
$R^{25}$=H, acyl or alkyl;
one of $R^2$ and $R^3$=H, and the other=F or OH, where the OH may be free or functionally modified; or $R^2$ and $R^3$ taken together=$OCH_2CH_2O$ or double bonded O (carbonyl); and
$R^4$=$(CH_2)_m$Xphenyl or $(CH_2)_pZ^2$, where X=O or $CH_2$; m=1–6; p=0–6; and

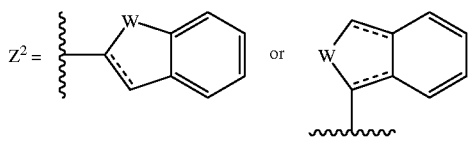

wherein:

W=O, $CH_2$, $CH_2CH_2$, or CH=CH; and wherein the phenyl component of $(CH_2)_m$Xphenyl and the six-membered ring component of $Z^2$ independently may be unsubstituted or substituted with halogen, $CH_3$, $CF_3$, CN, $OCH_3$, or acetyl;
with the proviso that when $R^{25}$=H, then $R^4$=$(CH_2)_pZ^2$ and the six-membered ring component of $Z^2$ is unsubstituted.

For purposes of the foregoing and following definitions, the term "alkyl" or "pharmaceutically acceptable ester moiety" means any ester moiety that would be suitable for therapeutic administration to a patient by any conventional means without significant deleterious health consequences. Similarly, the term "ophthalmically acceptable ester moiety" means any pharmaceutically acceptable ester moiety that would be suitable for ophthalmic application, i.e. non-toxic and non-irritating. Preferred are ophthalmically acceptable esters such as alkyl and alkylcycloalkyl esters of carboxylic acids. Most preferred are $C_2$–$C_5$ alkyl esters of carboxylic acids, and especially isopropyl esters.

The term "where the OH may be free or functionally modified" means either an OH group itself or or an OH group substituted with an alkyl or acyl group. The term "alkyl" or "alkyl group" includes straight or branched chain aliphatic hydrocarbon groups that are saturated, preferably having 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl. The term "acyl" or "acyl group" means an alkyl- or hydrogen-substituted carbonyl group (H—C=O or alkyl-C=O), where alkyl is defined as above. The term "halogen" means fluorine, chlorine, bromine, or iodine.

Preferred compounds of the present invention are those of formula III:

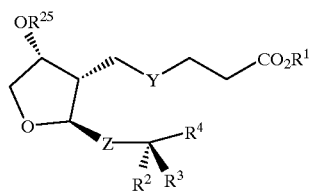

III wherein:

$R^1$=H, or $C_2$–$C_5$ linear or branched alkyl;
Y=cis $CH_2CH=CH$, cis $CH=CHCH_2$, or $CH_2CH_2CH_2$;
Z=C≡C, trans CH=CH, or $CH_2CH_2$;
$R^{25}$=H, acyl, or alkyl;
one of $R^2$ and $R^3$=H, and the other=F or OH, where the OH may be free or functionally modified; or $R^2$ and $R^3$ taken together=$OCH_2CH_2O$ or double bonded O (carbonyl); and
$R^4$=$(CH_2)_m$Xphenyl or $(CH_2)_pZ^2$, where X=O or $CH_2$; m=1–6; p=0–6; and

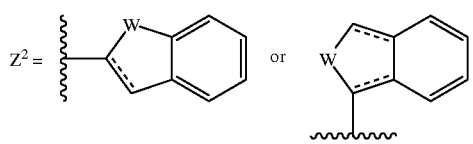

wherein:

W=O, $CH_2$, $CH_2CH_2$, or CH=CH; and
wherein the phenyl component of $(CH_2)_m$Xphenyl and the six-membered ring component of $Z^2$ independently may be unsubstituted or substituted with halogen, $CH_3$, $CF_3$, CN, $OCH_3$, or acetyl;
with the proviso that when $R^{25}$=H, then $R^4$=$(CH_2)_pZ^2$ and the six-membered ring component of $Z^2$ is unsubstituted.

With the exception of methyl (5Z,13E,15R)-9α-acetoxy-15-hydroxy-17-(3-trifluoromethylphenyl)-11-oxa-18,19,20-trinorprosta-5,13-dienoate and methyl (5Z,13E,15S)-9α-acetoxy-15-hydroxy-17-(3-trifluoromethylphenyl)-11 -oxa-18,19,20-trinorprosta-5,13-dienoate (syntheses of which have been reported by Verdoorn, et al., *S. African J. Chem.,* 40:134–138 (1987)), the $PGF_{2\alpha}$-type analogs useful in the present invention are believed to be novel. Related 11 -oxa PGFs outside the scope of the present invention are, however, known and their syntheses are described in the literature. The 11-oxa analogs of $PGF_{2\alpha}$ and $PGF_{2\beta}$ are disclosed in Hanessian, et al., *Carbohydrate Research,* 141:221–238 (1985); and Thiem et al., *Liebigs Ann. Chem.,* 2151–2164 (1985). Arndt, et al., *S. African J. Chem.,*

34:121–127 (1981), and U.S. Pat. No. 4,133,817, similarly disclose 11-oxa analogs of $PGF_{2\alpha}$. The entire contents of these references are hereby incorporated herein.

Most preferred among the compounds for the present invention are those of formula III wherein $R^{25}$ is C1–C5 linear or branched alkyl or acyl, and especially methyl; and wherein $R^{25}$=H, $R^4$=$(CH_2)_pZ^2$, p=0, $Z^2$ is as defined above and is unsubstituted, and W=O or $CH_2$.

In the foregoing illustrations, as well as those provided hereinafter, wavy line attachments indicate that the configuration may be either alpha ($\alpha$) or beta ($\beta$). The dashed lines on bonds between carbons, e.g. in the bicyclic structural formula for $Z^2$, indicate a single or double bond. Two solid lines present between carbons specify the configuration of the relevant double bond. Hatched lines indicate the $\alpha$ configuration, and a solid triangular line indicates the $\beta$ configuration.

In the following Examples 1–4, the following standard abbreviations are used: g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

Synthesis of (3aR, 4S, 6aR)-Hexahydro-2-oxofuro [3,4-b]furan-4-carboxaldehyde (11)

The compounds of this invention may be prepared from the compound (3aR, 4S, 6aR)-hexahydro-2-oxofuro[3,4-b] furan-4-carboxaldehyde (11), which is prepared from the readily available 1,2-O-isopropylidene-$\alpha$-D-xylofuranose (1) according to published methodology (Arndt, et al. *S. Afr. J. Chem.*, 34:121–127 (1981); U.S. Pat. No. 4,133,948). The following Scheme 1 outlines the synthetic route to (11).

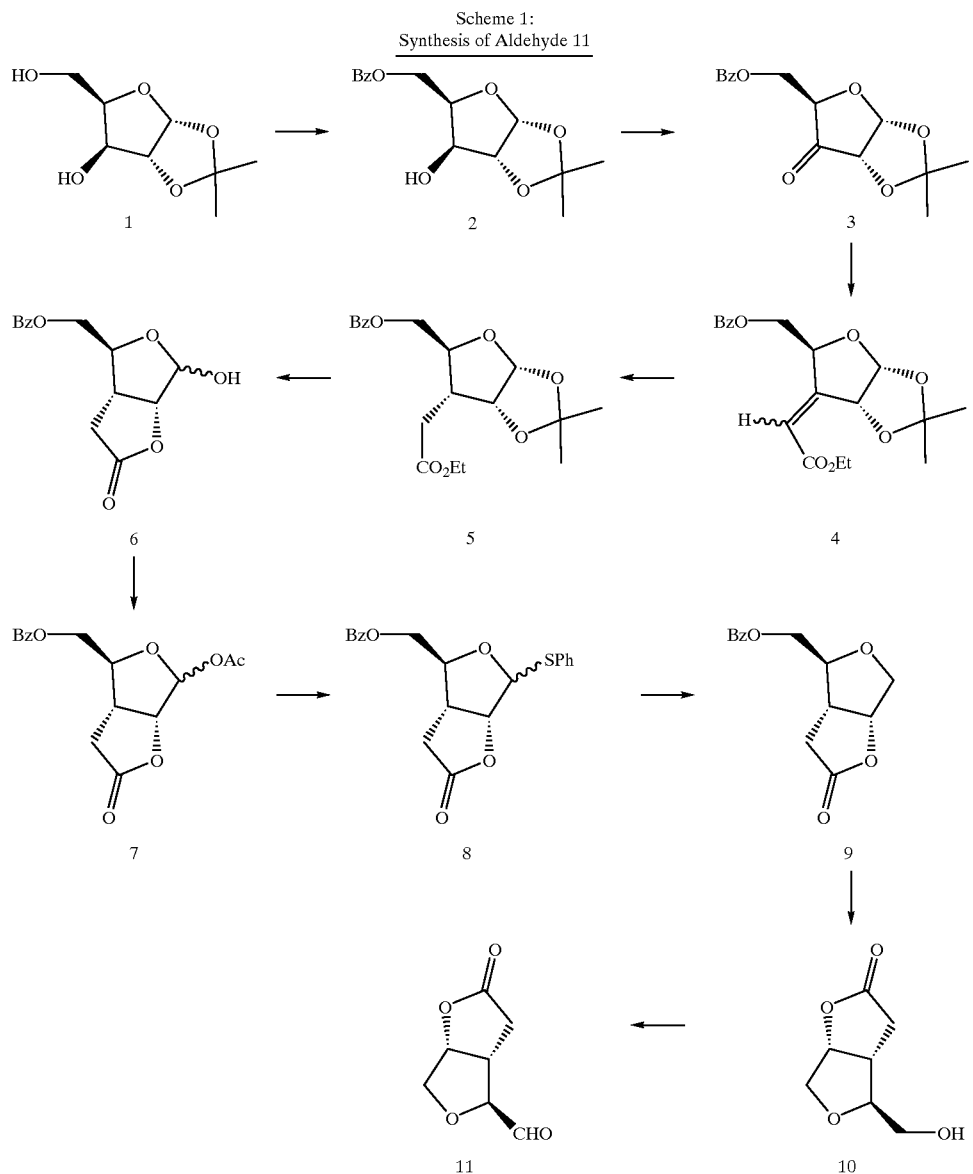

A: 5-O-Benzoyl-1,2-O-isopropylidene-α-D-xylofuranose (2)

A solution of 1,2-O-isopropylidene-α-D-xylofuranose 1 (30 g, 0.15 mol) in 360 mL of $CH_2Cl_2$ was cooled to 0° C. and to it was added 20 mL (0.23 mol) of pyridine and a catalytic amount (1.0 g) of N,N-dimethylaminopyridine. The resulting mixture was stirred at 0° C. for 10 min, at which time 20 mL (0.17 mol) benzoyl chloride was added to it dropwise over a period of 30 min. The reaction mixture was stirred at 0° C. for an additional 30 min and then quenched by the addition of 200 mL a saturated solution of $NH_4Cl$. The reaction was allowed to warm to room temperature, the layers were separated, and the aqueous layer was extracted with 3×50 mL of $CH_2Cl_2$. The combined organic extracts were washed with 3×50 mL of a 10% aqueous solution of $CuSO_4$, 2×50 mL of water and brine. The organic solution was dried over anhydrous $MgSO_4$, filtered and concentrated. The crude product mixture was purified by chromatography on silica gel to afford 44.3 g (95% yield) of 2 as a colorless liquid: $R_f$ 0.54 (60% EtOAc/hexane); $^1$H-NMR ($CDCl_3$) δ8.03 (m, 2H), 7.40–7.68 (m, 3H), 5.97 (d, 1H, J=3.6 Hz), 4.80 (m, 1H), 4.61 (d, 1H, J=3.4 Hz), 4.37 (m, 2H), 4.20 (s, broad, 1H), 3.35 (broad, 1H), 1.50 (s, 3H), 1.32 (s, 3H).

B: 5-O-Benzoyl-1,2-O-isopropylidene-α-D-erythropentofuranos-3-ulose (3)

A solution of oxalyl chloride (2.0 M in $CH_2Cl_2$, 113 mL, 0.22 mol) in 400 mL of anhydrous $CH_2Cl_2$ was cooled to −78° C. under a $N_2$ atmosphere. To this, a solution of dimethylsulfoxide (32 mL, 0,45 mol) in 50 mL of anhydrous $CH_2Cl_2$ was added dropwise over a period of 5 min. After the resulting solution had been stirred at the same temperature for 5 min, a solution of 2 (44.3 g, 0.15 mol) in 500 mL of anhydrous $CH_2Cl_2$ was added to it dropwise over a period of 15 min. Stirring was continued at −78° C. for an additional 15 min. Triethylamine (60 mL, 0.42 mol) was then added to the reaction mixture, and after a further 15 min at −78° C. the cold temperature bath was removed, and the stirring was continued for 10 min. The reaction was then quenched by the addition of 400 mL of water. The biphasic mixture was allowed to warm to room temperature and the layers were separated. The aqueous layer was extracted with 3×100 mL of $CH_2Cl_2$. The organic extracts were combined and washed with water (3×100 mL) and brine and was dried over anhydrous $Na_2SO_4$. Filtration and solvent removal afforded crude 3 (42.5 g, 96% yield) as a pale yellow solid, which was used in the next step without further purification: $^1$H-NMR ($CDCl_3$) δ7.97 (m, 2H), 7.40–7.65 (m, 3H), 6.14 (d, 1H, J=4.40 Hz), 4.69 (m, 2H), 4.44 (m, 2H), 1.15 (s, 3H), 1.43 (s, 3H).

C: (3aR, 4S, 6RS, 6aR)-4-(Benzoyloxy)methylhexahydro-6-hydroxyfuro[3,4-b]furan-2-one (6)

The crude sample of 3 (42.5 g, 0.15 mol), triethylphosphonoacetate (40.5 g, 0.18 mol) and lithium chloride (7.6 g, 0.18 mol) were combined and dissolved in 1.0 L of anhydrous THF. The solution was cooled to 0° C. and to it triethylamine (25.3 mL, 0.18 mol) was added dropwise. The resulting slurry was allowed to warm to room temperature gradually, and stirred under a $N_2$ atmosphere for 24 h. The reaction mixture was then poured into 500 mL of a 50% aqueous NaCl solution. The layers were separated and the aqueous layer was extracted with 2×200 mL of EtOAc. The combined organic extracts were dried over anhydrous $MgSO_4$. Filtration and solvent removal afforded 50 g of the crude enoate 4 as a mixture of two diastereomers which was used in the next step: $R_f$ 0.58 and 0.50 (minor and major isomers, respectively, 50% EtOAc/hexane).

To a suspension of 30–40 g of Raney-Ni (Aldrich, washed to neutrality with distilled water) in 750 mL of methanol the crude enoate 4 (50 g) from above was added, and the resulting mixture was hydrogenated at 65–70 psi, at room temperature in a Parr high-pressure reactor for 18 h. The reaction mixture was carefully filtered through a pad of celite. The solids were washed thoroughly with methanol. The filtrates were combined and evaporated, and the crude product mixture was purified by passage through a short pad of silica gel to afford 46.7 g (85% yield for two steps) of 5 as a colorless liquid. This material was carried onto the next step: $R_f$ 0.46 (50% EtOAc/hexane); $^1$H NMR ($CDCl_3$) δ 8.03 (m, 2H), 7.40–7.65 (m, 3H), 5.88 (d, J=3.6 Hz, 1H), 4.85 (m, 1H), 4.05–4.65 (m, 5H), 2.78 (m, 1H), 2.40 (m, 2H), 1.52 (s, 3H), 1.32 (s, 3H), 1.25 (t, J=7.15 Hz, 3H).

The acetonide 5 (46.7 g, 0.12 mol) obtained above was dissolved in 250 mL of a 4:1 mixture of glacial acetic acid and water, and the resulting solution was heated at 100° C. for 3.5 h. The reaction mixture was cooled to room temperature and the solvent was removed in vacuo. The residue was dissolved in 100 mL of toluene and the solution was concentrated to afford 39.6 g (quantitative yield) of 6 as pale yellow viscous liquid: $R_f$ 0.23 (50% EtOAc/hexane); $^1$H-NMR ($CDCl_3$) δ8.01 (m, 2H), 7.38–7.69 (m, 3H), 5.62 (s, 1H), 4.93 (d, 1H, J=6.02 Hz), 4.30–4.70 (m, 3H), 3.20 (m, 1H), 2.50–3.05 (m, 2H).

D: (3aR, 4S, 6RS, 6aR)-6-Acetyloxy-4-(benzoyloxy)methylhexahydrofuro[3,4-b]furan-2-one (7)

The lactone 6 (39.6 g, 0.14 mol) was dissolved in 70 mL of pyridine. To this solution 70 mL of acetic anhydride was added and the resulting mixture was stirred at room temperature for 20 h. The solvent was then evaporated and the residue was dissolved in 1.5 L of EtOAc. This solution was sequentially washed with 2×150 mL of water, 3×150 mL of a 0.25 N HCl solution water, 1×150 mL water and 1×100 mL brine. The organic layer was dried over anhydrous $MgSO_4$, filtered and concentrated. The crude product was isolated as a yellow solid which was titurated with hot ether to afford 29.0 g of a white crystalline solid which was found to be a single diastereomer of the acetate by $^1$H-NMR. The mother liquor was concentrated and purified by chromatography on silica gel to afford 6.7 g of a mixture of diastereomeric acetates as a yellow liquid. The combined yield of 7 being 87%: $R_f$0.3 (60% EtOAc/hexane); $^1$H-NMR ($CDCl_3$) δ (for major isomer only) 8.03 (m, 2H), 7.42–7.68 (m, 3H), 6.41 (s, 1H), 5.01 (d, 1H, J=6.3 Hz), 4.45 (s, broad, 3H), 3.22 (m, 1H), 2.90 (dd, 1H, J=14.4, 9.0 Hz), 2.62 (dd, 1H, J=14.4, 3.4 Hz), 2.03 (s, 3H).

E: (3aR, 4S, 6RS, 6aR)-4-(Benzoyloxy)methylhexahydro-6-phenylthiofuro[3,4-b]furan-2-one (8)

To a suspension of 7 (35.7 g, 0.11 mol) and thiophenol (14.8 mL, 0.13 mol) in 220 mL of a 4:1 mixture of anhydrous toluene and dichloromethane at room temperature, boron trifluoride etherate (6.9 mL, 0.05 mol) was added dropwise. The resulting mixture was stirred at the same temperature for 6.5 h and then carefully poured into a biphasic mixture of 1000 mL of EtOAc and 100 mL of a saturated aqueous solution of $NaHCO_3$ (sat. $NaHCO_3$). The layers were separated and the organic layer was washed with 2×100 mL of saturated $NaHCO_3$, 100 mL of water and 100 mL of brine. The organic layer was dried over anhydrous $MgSO_4$, filtered and concentrated to afford a yellow liquid. This material was dissolved in 50 mL of $CHCl_3$, and to it was added 200 mL of ether and 50 mL of hexane. The resulting solution was briefly cooled to −78° C. to induce crystallization. White powdery solid formed which was filtered off and washed with cold ether to afford 29.6 g of 8

(72% yield) as a mixture of two diastereomers: $R_f$ 0.70 and 0.53 (minor and major isomers, respectively, 60% EtOAc/hexane); $^1$H-NMR (CDCl$_3$) δ (for major isomer only) 8.01 (m, 2H), 7.42–7.70 (m, 5H), 7.27 (m, 3H), 5.89 (d, 1H, J=5.2 Hz), 5.29 (dd, 1H, J=7.7, 5.2 Hz), 4.55 (m, 2H), 4.48 (m, 1H), 2.60–3.12 (m, 3H).

F:(3aR, 4S, 6aR)-4-(Bezoyloxy)methylhexahydrofuro[3,4-b]furan-2-one (9)

A 3-neck, 1000 mL round-bottom flask, equipped for overhead mechanical stirring, was charged with 29.6 g of 8 (80 mmol), 500 mL of ethanol and approximately 30 g of Raney-Ni (Aldrich, which had been washed to neutrality with distilled water). The resulting slurry was heated at reflux for 5 h while stirring vigorously. The reaction mixture was then cooled to room temperature, and the solids were carefully filtered off through a pad of celite. The residue was washed thoroughly with ethanol, and the combined filtrates were concentrated to afford a yellow solid which was purified by chromatography on silica gel to afford 7.63 g (36% yield) of 9 as a white solid. A small sample was recrystallized from acetone/hexane to afford colorless needles: mp 89.5–90.0° C.; $[α]_D^{22}$+3.18 (c=0.8 in CHCl$_3$); $R_f$ 0.36 (60% EtOAc/hexane); $^1$H-NMR (CDCl$_3$) δ8.01 (m, 2H), 7.40–7.65 (m, 3H), 5.15 (m, 1H), 4.41 (m, 2H), 4.05–4.32 (m, 3H), 2.80–3.05 (m, 2H), 2.56 (d, 1H, J=15.7 Hz); MS m/z at 263 for (M+H)$^+$.

G:(3aR, 4S, 6aR)-Hexahydro-2-oxofuro[3,4-b]furan-4-carboxaldehyde (11)

To a solution of the benzoate 9 (2.63 g, 10.0 mmol) in 50 mL of warm methanol was added 1.4 g (10.0 mmol) of solid K$_2$CO$_3$. The resulting slurry was stirred at room temperature for 2.5 h, at which time 150 mL of water was added and the mixture was treated with Amberlyst-15 (purified and activated) until the solution was at pH 2–3. The resin was filtered and washed with 50 mL of water, and the filtrates were combined and concentrated to approximately 200 mL. This solution was extracted with 3×50 mL of EtOAc, the organic extracts were discarded and the aqueous phase was evaporated in vacuo. The residue was taken up in 50 mL of toluene and the solvent was evaporated; this drying procedure was repeated twice. The product hydroxylactone 10 thus obtained (1.64 g, 95% yield) was isolated as a pale yellow liquid. This material was used without further purification: $^1$H-NMR (d$_6$-DMSO) δ (crude sample) 5.12 (m, 1H), 4.81 (t, 1H, J=5.6 Hz, OH), 3.98 (dd, 1H, J=10.3, 4.1 Hz), 3.85 (d, 1H, J=10.5 Hz), 3.75 (m, 1H), 3.44 (m, 2H), 2.85 (m, 2H), 2.48 (m, 1H).

A solution of oxalyl chloride (2.0 M in CH$_2$Cl$_2$, 5.4 mL, 10.8 mmol) in 25 mL anhydrous CH$_2$Cl$_2$ was cooled to −78° C. under a N$_2$ atmosphere. To this, a solution of DMSO (1.5 mL, 21.6 mmol) in 5.0 mL of CH$_2$Cl$_2$ was added dropwise. The resulting mixture was stirred for 5 min, and then a solution of the hydroxylactone 10 obtained above (1.14 g, 7.21 mmol) in 50 mL of anhydrous CH$_2$Cl$_2$ was added dropwise. After 15 min at −78° C., triethylamine (2.85 mL, 20.2 mmol) was added to the reaction and stirring was continued for an additional 15 min at −78° C. The reaction was then allowed to warm to room temperature and filtered through a pad of celite. The filter cake was washed with CH$_2$Cl$_2$, the filtrates were combined and concentrated to approximately 10 mL; this solution was applied to a column of silica gel for chromatographic purification. The aldehyde 11 (0.9 g, 80% yield) was isolated as a colorless liquid: R$_f$ 0.6 (acetone); $^1$H-NMR (CDCl$_3$) δ 9.71 (s, 1H), 5.10 (m, 1H), 4.24 (m, 1H), 3.65–3.89 (m, 2H), 2.96 (m, 1H), 2.64 (m, 1H), 1.85 (m, 1H).

EXAMPLE 2

Synthesis of Isopropyl [2R(1E,3R),3S(5Z),4R]-7-[Tetrahydro-2-[4-(3-chlorophenoxy)-3-hydroxy-1-butenyl]-4-methoxy-3-furanyl]-5-heptenoate (IV)

Compound IV may be prepared according to the method described by the following Scheme 2.

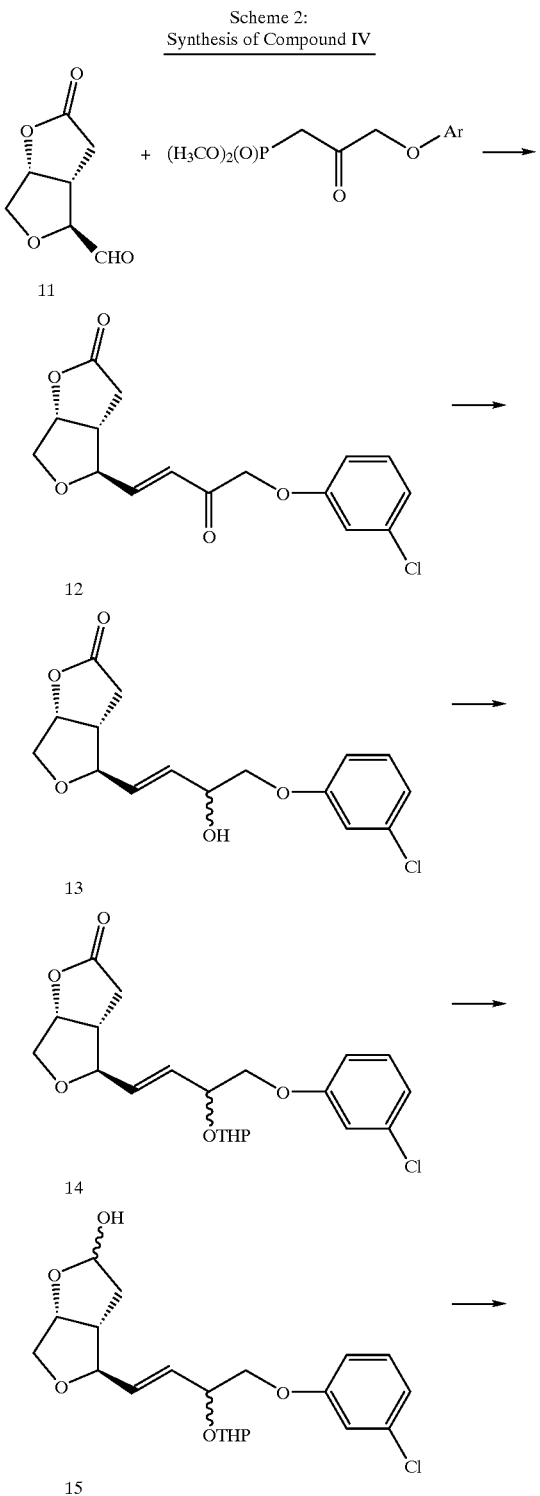

Scheme 2:
Synthesis of Compound IV

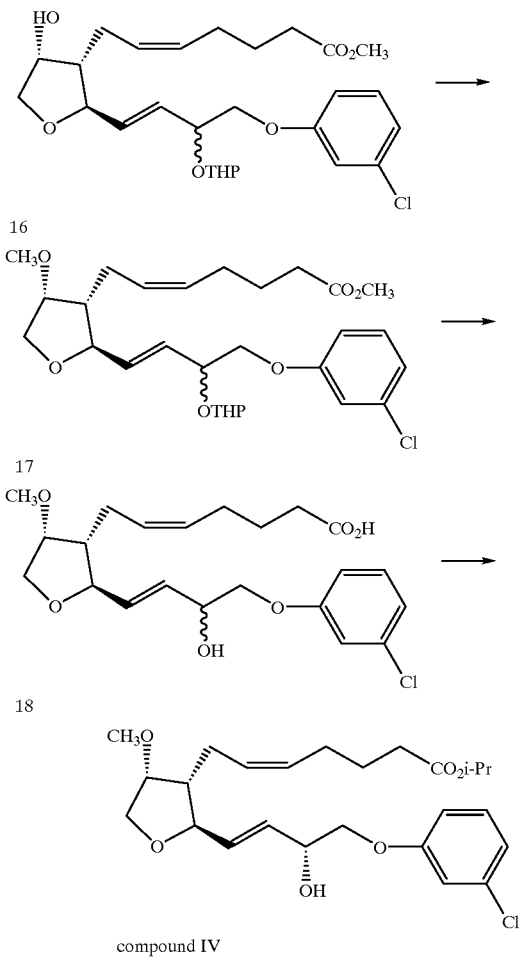

compound IV

A:[3aR, 4R(1E), 6aR]-4-[4-(3-Chlorophenoxy)-3-oxo-1-butenyl]hexahydrofuro[3,4-b]furan-2-one (12)

A solution of dimethyl-3-(3-chlorophenoxy)-2-oxopropylphosphonate (2.34 g, 8 mmol) and LiCl (0.29 g, 6.9 mmol) in 15 mL of anhydrous THF was cooled to 0° C. under $N_2$ atmosphere and to it triethylamine (0.97 mL, 6.9 mmol) was added dropwise. A white slurry formed, which was stirred for 3 min at 0° C., at which time a solution of the aldehyde 11 (0.9 g, 5.76 mmol) in 15 mL of anhydrous THF was added to it. The resulting mixture was stirred at 0° C. for 1 h, and then partitioned between 100 mL of water and 250 mL of EtOAc. The layers were separated and the organic phase was washed with water and brine, and dried ($MgSO_4$). Filtration and solvent removal afforded a yellow liquid which was purified by chromatography on silica gel to yield 1.13 g of the enone 12 (60% yield) as a colorless, viscous liquid: $R_f$ 0.29 (60% EtOAc/hexane); $^1$H-NMR (CDCl$_3$) δ 7.22 (m, 1H), 6.85–7.08 (m, 3H), 6.79 (m, 1H), 6.65 (dd, 1H, J=16.2, 1.6 Hz), 5.10 (m, 1H), 4.69 (s, 2H), 4.38 (m, 1H), 4.10 (m, 2H), 2.88 (m, 2H), 2.57 (m, 1H).

B: [3aR, 4R(1E,3RS), 6aR]-4-[4-(3-Chlorophenoxy)-3-hydroxy-1-butenyl]hexahydrofuro[3,4-b]furan-2-one (13)

A mixture of 12 (1.0 g, 3.10 mmol) and CeCl$_3$.7H$_2$O (2.3 g, 6.2 mmol) was taken up in a mixture of CH$_3$OH (25 mL) and CHCl$_3$ (10 mL), and the solution was cooled to 0° C. To this cold solution NaBH$_4$ (0.23 g, 6.2 mmol) was added in small portions over a period of 5 min. (CAUTION: vigorous hydrogen gas evolution occurs). The resulting mixture was stirred for an additional 3 min at 0° C., and then poured into 100 mL of 0.5 N HCl solution. The aqueous solution was extracted with 3×50 mL of CHCl$_3$. The organic extracts were combined and washed with 3×50 mL of water and brine, and dried over anhydrous MgSO$_4$. Filtration and solvent removal afforded an oil which was purified by silica gel chromatography to give 0.71 g (70% yield) of 13 (a diastereomeric mixture of alcohols) as a colorless liquid: $R_f$ 0.14 (60% EtOAc/hexanes); $^1$H-NMR (CDCl$_3$) δ 7.21 (m, 1H), 6.95 (m, 2H), 6.78 (m, 1H), 5.89 (s, broad, 2H), 5.11 (m, 1H), 4.56 (m, 1H), 4.20 (m, 2H), 4.01 (m, 2H), 3.89 (m, 1H), 2.85 (m, 2H), 2.57 (m, 2H); $^{13}$C-NMR (CDCl$_3$) δ175.62 (C=O), 158.96 (O—Ar), 134.93 (Cl—Ar), 130.95 and 130.80 (CH), 130.33 (CH), 129.86 and 129.75 (CH), 121.55 (CH), 115.02 (CH), 113.00 (CH), 84.57 and 84.51 (CH), 84.07 (CH), 72.48 (CH$_2$), 71.68 (CH$_2$), 69.82 and 69.76 (CH), 44.80 (CH), 32.49 (CH$_2$).

C:[3aR, 4R(1E,3RS), 6aR]-4-[4-(3-Chlorophenoxy)-3-(tetrahydropyran-2-yl)oxy-1-butenyl]-hexahydrofuro[3,4-b]furan-2-one (14)

A solution of 13 (0.71 g, 2.19 mmol) in 20 mL of CH$_2$Cl$_2$ was cooled to 0° C. To this 0.5 mL (4.38 mmol) of 3,4-dihydro-2H-pyran was added followed by a catalytic amount of p-toluenesulfonic acid (10 mg). The reaction was stirred at 0° C. for 15 min and then quenched by the addition of 10 mL of a saturated aqueous solution of NaHCO$_3$. The layers were separated and the aqueous layer was extracted with 2×10 mL of dichloromethane. The combined organic extracts were dried (MgSO$_4$), filtered and concentrated. The product 14 (0.78 g, 91% yield) was isolated as a colorless liquid after chromatography of the crude on silica gel: $R_f$ 0.28 (60% EtOAc/hexane).

D:Methyl [2R(1E,3RS), 3S(5Z), 4R]-7-[Tetrahydro-2-[4-(3-chlorophenoxy)-3-(tetrahydropyran-2-yl)oxy-1-butenyl]4-hydroxy-3-furanyl]-5-heptenoate (16)

A solution of the lactone 14 (0.78 g, 1.9 mmol) in 20 mL of anhydrous THF was cooled to –78° C. under a N$_2$ atmosphere, and diisobutylaluminum hydride (DIBAL-H, 1.9 mL, 1.5 M in toluene, 2.8 mmol) was added to it dropwise. The resulting mixture was stirred at –78° C. for 1.5 h and then quenched at the same temperature by the careful addition of 5 mL of methanol. The mixture was allowed to warm to room temperature, diluted with 50 mL of EtOAc and treated with 100 mL of a saturated, aqueous potassium sodium tartrate solution, with vigorous stirring, for 1 h. The layers were separated and the aqueous layer was extracted with 3×10 mL of EtOAc. The combined organic extracts were dried (MgSO$_4$), filtered and concentrated. The crude product thus obtained was purified by passage through a short pad of silica gel to afford the intermediate lactol 15 (0.68 g, 87% yield) as a colorless liquid: $R_f$ 0.15 (60% EtOAc/hexane).

To a suspension of (4-carboxybutyl)triphenylphosphonium bromide (2.2 g, 4.9 mmol) in 20 mL anhydrous THF at 0° C., potassium tert-butoxide (t-BuOK, 10.0 mL, 1.0 M THF, 10.0 mmol) was added dropwise and the mixture was stirred at 0° C. for 30 min. A solution of the lactol 15 obtained above (0.68 g, 1.65 mmol) in 50 mL of THF was then added to it dropwise. The resulting mixture was allowed to warm to room temperature and was stirred at that temperature for 16 h. The reaction was quenched by pouring it into a saturated aqueous solution of ammonium chloride (50 mL) which had been acidified to pH 2–3 with dilute aqueous HCl solution. The mixture was extracted with EtOAc (5×25 mL), and the combined organic extracts were washed with water (1×25 mL) and brine (1×25 mL) and dried over anhydrous Na$_2$SO$_4$. The solution was filtered, concentrated to approximately 10 mL and then cooled to 0°

C. This solution was treated with an excess of ethereal diazomethane at 0° C. The excess diazomethane was evaporated off by bubbling N₂ through the solution for 1 h. The resulting pale yellow solution was concentrated and applied to a column of silica gel for purification by chromatography. The methyl ester 16 (0.38 g, 50% yield, mixture of diastereomers) was isolated as a colorless liquid: R_f 0.27 (60% EtOAc/hexane).

E: Isopropyl [2R(1E,3R),3S(5Z),4R]-7-[Tetrahydro-2-[4-(3-chlorophenoxy)-3-hydroxy-1-butenyl]-4-methoxy-3-furanyl]-5-heptenoate (IV)

Treatment of compound 16 with methyl trifluoromethanesulfonate in the presence of 2,6-bis-t-butylpyrdine affords the methoxy compound 17. The removal of the protecting group with aqueous HCl, followed by saponification, and treatment of the resulting carboxylic acid 18 with isopropyl iodide in the presence of DBU affords the desired compound IV.

Synthesis of V

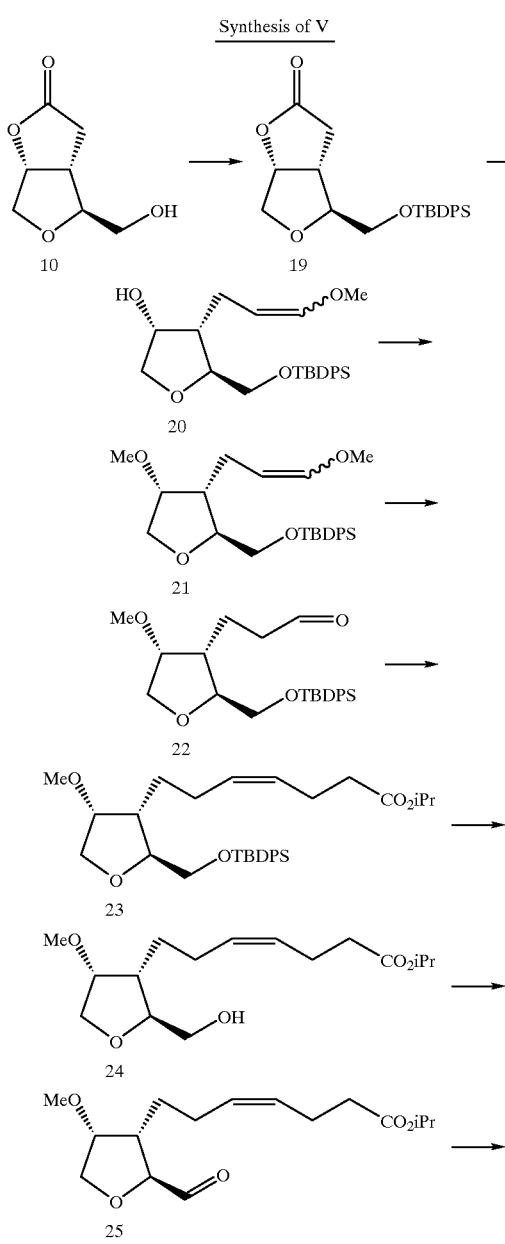

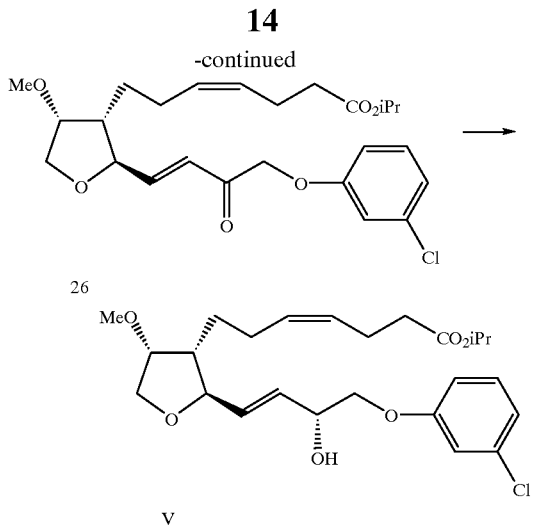

(3aR,4S,6aR)-4-(tert-Butyldiphenylsilyloxy)methylhexahydrofuro[3,4-b]furan-2-one (19)

A mixture of alcohol 10 (5.0 g, 31.6 mmol) and imidazole (4.3 g, 63.2 mmol) was dissolved in 100 mL of anhydrous DMF. To this solution tert-butyldiphenylsilyl chloride (10.4 g, 38.0 mmol) was added and the resulting mixture was stirred at room temperature for 14 h. The solvent was evaporated and the residue was taken up in 100 mL of EtOAc, washed with water (2×50 mL), dilute aqueous solution of HCl (2×50 mL) and brine and dried (MgSO4). The solvent was evaporated and the crude was purified by chromatography on silica gel to afford 19 (12.4 g, quantitative yield) as a white solid: R_f 0.6 (60% EtOAc/hexanes). ¹H-NMR (CDCl₃) δ7.65 (m, 4H), 7.42 (m, 6H), 5.10 (m, 1H), 4.25 (dd, J=12, 4 Hz, 1H), 4.05 (dd, J=12, 2 Hz, 1H), 3.85 (m, 1H), 3.75 (m, 2H), 3.00 (m, 1H), 2.82 (dd, J=16, 7 Hz, 1H), 2.45 (dd, J=16, 2 Hz, 1H), 1.05 (s, 9H).

[2S,3S(2EZ),4R]-2-[(t-butyldiphenylsiloxy)methyl]-4-hydroxy-3-(3-methoxyprop-2-en-1-yl)tetrahydrofuran (20)

A solution of the lactone 19 (5.7 g, 14.5 mmol) in 150 mL of anhydrous THF was cooled to −78° C. under an inert atmosphere, and to it DIBAL-H (14.5 mL, 1.5 M in toluene, 21.7 mmol) was added dropwise. The resulting mixture was stirred at −78° C. for 1.5 h and was then quenched at the same temperature by the addition of 5 mL of methanol. The reaction was warmed to room temperature, an equal volume of a saturated aqueous solution of potassium sodium tartrate was added to it, and the resulting slurry was stirred at room temperature for 1 h. The layers were separated, and the aqueous layer was extracted with 3×25 mL of EtOAc. The organic layers were combined and washed with brine and dried (MgSO₄). The solution was filtered and concentrated and the crude was purified by passage through a short column of silica gel to afford the intermediate lactol (5.6 g, quantitative yield) as a colorless oil: R_f 0.5 (60% EtOAc/hexanes).

A suspension of (methoxymethyl)triphenylphosphonium chloride (2.5 g, 7.5 mmol) in 70 mL of dry THF was cooled to 0° C. under a N₂ atmosphere. To this solution potassium tert-butoxide (t-BuOK, 9.0 mL, 1.0 M in THF, 9.0 mmol) was added dropwise, and stirring was continued at 0° C. for an additional 20 min. At this time a solution of the lactol obtained above (1.0 g, 2.5 mmol) in 30 mL of dry THF was added to it, and the resulting mixture was stirred at 0° C. for 1.5 h. The reaction was then worked up by pouring it into 50 mL of a saturated aqueous solution of KH₂PO₄, the layers were separated and aqueous layer was extracted with 3×25 mL of EtOAc. The combined organic layers were washed with water and brine, and dried (MgSO$_4$); solvent removal and chromatography of the crude on silica afforded the enol ether 20 (0.89 g, 83% yield) as a colorless liquid: R$_f$0.6 (60% EtOAc/hexanes).

Isopropyl [2R(1E,3R),3S(4Z),4R]-7-[Tetrahydro-2-[4-(3-chlorophenoxy)-3-hydroxy-1-butenyl]-4-hydroxy-3-furanyl]-4-heptenoate (V)

Methylation of alcohol 20 using methyl trifluoromethane-sulfonate and 2,6-di-t-butylpyridine in dichloromethane affords methyl ether 21, which is deprotected to aldehyde 22 treatment with p-toluenesulfonic acid monohydrate in THF/water at 65° C. Wittig condensation of 22 with Ph$_3$P$^+$(CH$_2$)$_3$CO$_2$H Br$^-$ in THF in the presence of potassium t-butoxide affords, after alkylation of the resultant carboxylic acid with isopropyl iodide/DBU in acetone, ester 23. Desilylation to 24 is accomplished using tetra-n-butylammonium fluoride in THF; oxidation of 24 under Swern conditions (oxalyl chloride, DMSO, Net$_3$, CH$_2$Cl$_2$, -78° C.) provides aldehyde 25. Condensation of this aldehyde with dimethyl 3-(3-chlorophenoxy)-2-oxopropylphosphonate in the presence of NEt$_3$ and LiCl in THF yields enone 26, which is reduced with (-)-B-chlorodiisopinocampheylborane in THF at 0° C. to afford, after separation of carbon-15 alcohol diastereomers via silica gel chromatography, product V.

The substituted tetrahydrofurans of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between about 4.5 to about 8.0, preferably between about 5.0 and about 7.5. The compounds are preferably formulated as between about 0.0005 to about 0.03 wt % and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents, and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil); cyclodextrin; or other agents known to those skilled in the art. Such co-solvents are typically employed at a level between about 0.01% and about 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of substituted tetrahydrofurans of the present invention include the following Example 4:

| Ingredient | Amount (wt %) |
| --- | --- |
| Compound V | 0.01 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor ® EL | 0.1 |
| Benzalkonium chloride | 0.01 |
| HCl and/or NaOH | q.s. pH 7.3–7.4 |
| Purified water | q.s. 100% |

What is claimed is:

1. A method of treating glaucoma or ocular hypertension in a patient, which comprises administering to the patient a pharmaceutically effective amount of a compound of formula (II):

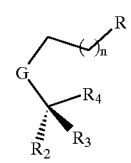

(II)

wherein:

R=ophthalmically acceptable ester moiety, $CO_2R^1$, $CONR^7R^8$, $CH_2OR^9$, or $CH_2NR^{10}R^{11}$ where $R^1$=H or cationic salt moiety; $R^7$ and $R^8$ are the same or different=H or alkyl; $R^9$=H, acyl, or alkyl; $R^{10}$ and $R^{11}$ are the same or different=H, acyl, or alkyl; with the proviso that if one of $R^{10}$ and $R^{11}$=acyl, then the other=H or alkyl;

n=0, 2;

G is:

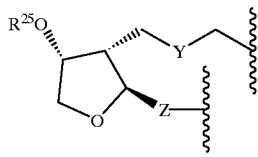

(i)

wherein:

Y=cis $CH_2CH=CH$, cis $CH=CHCH_2$, or $CH_2CH_2CH_2$;

Z=$C\equiv C$ trans $CH=CH$, or $CH_2CH_2$;

$R^{25}$=H, acyl, or alkyl;

one of $R^2$ and $R^3$=H, and the other=F or OH, where the OH may be free or functionally modified; or $R^2$ and $R^3$ taken together=$OCH_2CH_2O$ or double bonded O (carbonyl); and $R^4$=$(CH_2)_m$Xphenyl or $(CH_2)_pZ^2$, where X=O or $CH_2$; m=1–6; p=0–6;

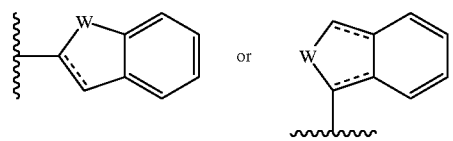

or wherein:

W=O, $CH_2$, $CH_2CH_2$, or $CH=CH$; and wherein the phenyl component of $(CH_2)_m$Xphenyl and the six-membered ring component of $Z^2$ independently may be unsubstituted or substituted with halogen, $CH_3$, $CF_3$, CN, $OCH_3$, or acetyl;

with the proviso that when $R^{25}$=H, then $R^4$=$(CH_2)_pZ^2$ and the six-membered ring component of $Z^2$ is unsubstituted.

2. The method of claim 1, where the compound is administered topically.

3. The method of claim 2, wherein the compound is administered as a solution, suspension, or emulsion.

4. The method of claim 2, wherein R is an ophthalmically acceptable ester selected from the group consisting of: isopropyl and neopentyl esters of carboxylic acids, and $R^{25}$ is $C_1$–$C_5$ linear alkyl.

5. The method of claim 4, wherein $R_4$=$(CH_2)_m$X phenyl, where X=O or $CH_2$, m=1–6, and the phenyl is either unsubstituted or substituted with a substituent selected from the group consisting of: halogen and $CF_3$.

6. The method of claim 5, wherein the compound is:

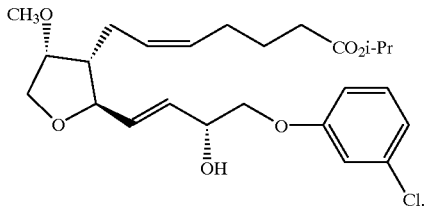

7. The method of claim 3, wherein the compound is:

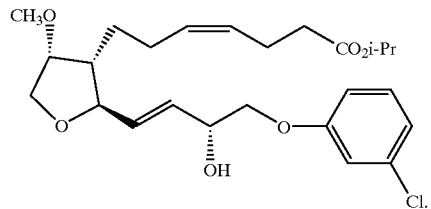

8. The method of claim 3, wherein the concentration of the compound is between about 0.00003 to about 0.5 weight percent.

9. The method of claim 8, wherein the concentration of the compound is between about 0.0005 to about 0.03 weight percent.

10. The method of claim 9, wherein the concentration of the compound is between about 0.001 and about 0.01 weight percent.

11. A compound of formula (II):

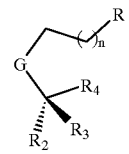

(II)

wherein:

R=a pharmaceutically acceptable ester moiety, $CO_2R^1$, $CONR^7R^8$, $CH_2OR^9$, or $CH_2NR^{10}OR^{11}$, wherein $R^1$=H or cationic salt moiety; $R^7$ and $R^8$ are the same or different=H or alkyl; $R^9$=H, acyl, or alkyl; $R^{10}$ and $R^{11}$ are the same or different=H, acyl, or alkyl; with the proviso that if one of $R^{10}$ and $R^{11}$=acyl, then the other=H or alkyl;

n=0, 2;

G is:

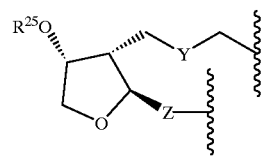

(i)

wherein:

Y=cis $CH_2CH=CH$, cis $CH=CHCH_2$, or $CH_2CH_2CH_2$;

Z=$C\equiv C$, trans $CH=CH$, $CH_2CH_2$;

$R^{25}$=H, alkyl, or acyl;

one of $R^2$ and $R^3$=H, and the other=F or OH, where the OH may be free or functionally modified; or $R^2$ and $R^3$ taken together=$OCH_2CH_2O$ or double bonded O (carbonyl); and $R^4$=$(CH_2)_m$X phenyl or $(CH_2)_pZ^2$, where X=O or $CH_2$, m=1–6; p=0–6;

$Z^2 =$ 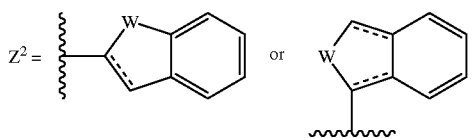 or 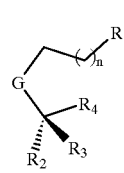

wherein:

W=O, CH$_2$, CH$_2$CH$_2$, or CH=CH; and wherein the phenyl component of (CH$_2$)$_m$Xphenyl and the six-membered ring component of Z$^2$ independently may be unsubstituted or substituted with halogen, CH$_3$, CF$_3$, CN, OCH$_3$, or acetyl;

with the proviso that when R$^{25}$=H, then R$^4$=(CH$_2$)$_p$Z$^2$ and the six-membered ring component of Z$^2$ is unsubstituted;

with the further proviso that the following compounds be excluded:

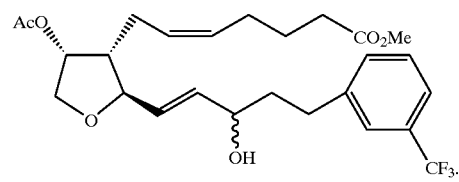

12. The compound of claim 11, having the following structure:

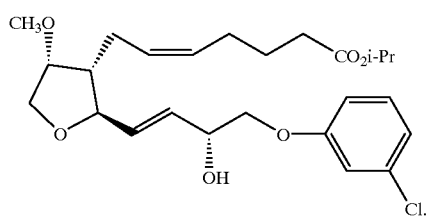

13. The compound of claim 11, having the following structure:

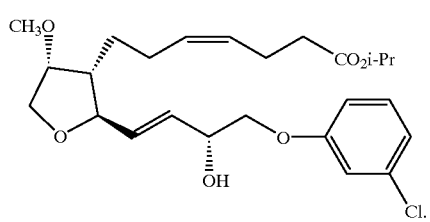

14. An ophthalmic composition for the treatment of glaucoma and ocular hypertension, comprising a compound of formula (II):

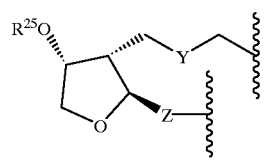 (II)

wherein:

R=ophthalmically acceptable ester moiety, CO$_2$R$^1$, CONR$^7$R$^8$, CH$_2$O R$^9$, or CH$_2$NR$^{10}$R$^{11}$ where R$^1$=H or cationic salt; R$^7$ and R$^8$ are the same or different=H or alkyl; R$^9$=H, acyl, or alkyl; R$^{10}$ and R$^{11}$ are the same or different=H, acyl, or alkyl; with the proviso that if one of R$^{10}$ and R$^{11}$=acyl, then the other=H or alkyl;

n=0, 2;

G is:

(i)

wherein:

Y=cis CH$_2$CH=CH, cis CH=CHCH$_2$, or CH$_2$CH$_2$CH$_2$;

Z=C≡C, trans CH=CH, or CH$_2$CH$_2$;

R$^{25}$=H, alkyl, or acyl;

one of R$^2$ and R$^3$=H, and the other=F or OH, where the OH may be free or functionally modified; or R$^2$ and R$^3$ taken together=OCH$_2$CH$_2$O or double bonded O (carbonyl); and R$^4$=(CH$_2$)$_m$Xphenyl or (CH$_2$)$_p$Z$^2$, where X=O or CH$_2$; m=1–6; p=0–6; and $Z^2 =$ 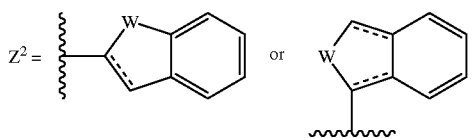 or 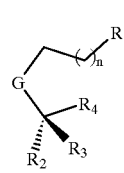

wherein:

W=O, CH$_2$, CH$_2$CH$_2$, or CH=CH; and wherein the phenyl component of (CH$_2$)$_m$Xphenyl and the six-membered ring component of Z$^2$ independently may be unsubstituted or substituted with halogen, CH$_3$, CF$_3$, CN, OCH$_3$, or acetyl;

with the proviso that when R$^{25}$=H, then R$^4$=(CH$_2$)$_p$Z$^2$ and the six-membered ring component of Z$^2$ is unsubstituted;

and an ophthalmically acceptable vehicle therefor.

15. The ophthalmic composition of claim 14, wherein the compound is:
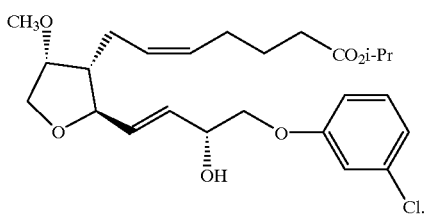
16. The ophthalmic composition of claim 14, wherein the compound is:
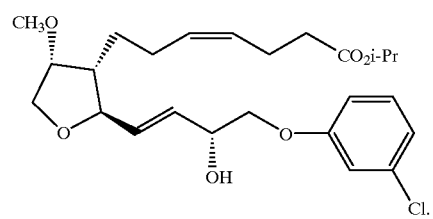
* * * * *

UNITED STATES PATENT AND TRADEMARK OFFICE
CERTIFICATE OF CORRECTION

PATENT NO. : 6,025,392
DATED : February 15, 2000
INVENTOR(S) : Robert D. Selliah; Mark R. Hellberg; Peter G. Klimko; Verney L. Sallee; Paul W. Zinke It is certified that error appears in the above-identified patent and that said Letters Patent is hereby corrected as shown below:

Column 17, line 24, after "p = 0-6;" insert --and $Z^2$ = --.

Signed and Sealed this

Twenty-fourth Day of April, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.   : 6,025,392
DATED        : February 15, 2000
INVENTOR(S)  : Robert D. Selliah et al.

It is certified that error appears in the above-identified patent and that said Letters Patent is hereby corrected as shown below:

<u>Column 18,</u>
Line 37, change "$CH_2NR^{10}OR^{11}$" to -- $CH_2NR^{10}R^{11}$ --

Signed and Sealed this

Thirty-first Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.   : 6,025,392
DATED        : February 15, 2000
INVENTOR(S)  : Robert D. Selliah et al.

It is certified that error appears in the above-identified patent and that said Letters Patent is hereby corrected as shown below:

Column 18,
Line 37, change "$CH_2NR^{10}OR^{11}$" to -- $CH_2NR^{10}R^{11}$ --

Signed and Sealed this

Twenty-first Day of January, 2003

JAMES E. ROGAN
*Director of the United States Patent and Trademark Office*